United States Patent
Canestraro

(10) Patent No.: US 12,351,363 B2
(45) Date of Patent: Jul. 8, 2025

(54) SUPPORT DEVICE FOR SUPPORTING A PLURALITY OF CONTAINERS FOR PHARMACEUTICAL USE TO BE HANDLED IN A PROCESSING LINE

(71) Applicant: NUOVA OMPI S.R.L. Unipersonale, Piombino Dese (IT)

(72) Inventor: Marco Canestraro, Carmignano di Brenta (IT)

(73) Assignee: NUOVA OMPI S.R.L. UNIPERSONALE, Piombino Dese (IT)

( * ) Notice: Subject to any disclaimer, the term of this patent is extended or adjusted under 35 U.S.C. 154(b) by 13 days.

(21) Appl. No.: 18/356,691

(22) Filed: Jul. 21, 2023

(65) Prior Publication Data

US 2024/0025597 A1    Jan. 25, 2024

(30) Foreign Application Priority Data

Jul. 25, 2022    (IT) .......................... 102022000015549

(51) Int. Cl.
*B65D 25/10*    (2006.01)
(52) U.S. Cl.
CPC .................................. *B65D 25/108* (2013.01)
(58) Field of Classification Search
CPC ............. B65D 25/108; B01L 2200/025; B01L 2300/0829; B01L 9/06; B65B 3/003; B65B 43/54; B65B 65/00; A61M 5/008
See application file for complete search history.

(56) References Cited

U.S. PATENT DOCUMENTS

| | | | |
|---|---|---|---|
| 6,286,678 B1 * | 9/2001 | Petrek | B01L 9/543 422/526 |
| 10,207,832 B2 | 2/2019 | Narvekar et al. | |
| 2009/0100802 A1 * | 4/2009 | Bush | A61M 5/002 53/434 |
| 2018/0057249 A1 | 3/2018 | Bertolin | |
| 2018/0208377 A1 | 7/2018 | Kloke et al. | |
| 2019/0125473 A1 | 5/2019 | Togashi et al. | |
| 2019/0343721 A1 | 11/2019 | Komann et al. | |
| 2021/0220221 A1 | 7/2021 | Komann et al. | |

FOREIGN PATENT DOCUMENTS

| | | |
|---|---|---|
| DE | 202016107209 U1 | 5/2018 |
| WO | 2018020505 A1 | 2/2018 |

* cited by examiner

*Primary Examiner* — Andrew D Perreault
(74) *Attorney, Agent, or Firm* — Husch Blackwell LLP

(57) ABSTRACT

A support device for supporting a plurality of containers for pharmaceutical use to be handled in a processing line includes a body having an upper surface, a lower surface, a perimeter portion and a central portion delimited by the perimeter portion. The central portion includes a plurality of housing seats configured to house the containers and a plurality of separating elements interposed between adjacent housing seats, wherein at least two of the separating elements are hollow and each of the at least two separating elements includes, at the upper surface, a through opening. An assembly including the support device and a second support device for closing containers and having coupling elements configured for insertion through the through openings of the separating elements is also disclosed.

10 Claims, 5 Drawing Sheets

SUPPORT DEVICE FOR SUPPORTING A PLURALITY OF CONTAINERS FOR PHARMACEUTICAL USE TO BE HANDLED IN A PROCESSING LINE

CROSS REFERENCES

This application is a U.S. Application claiming priority to Italian Application No. 102022000015549 filed on Jul. 25, 2022, the disclosure of which is incorporated herein by reference in its entirety.

TECHNICAL FIELD

The present disclosure relates to a support device for supporting a plurality of containers for pharmaceutical use to be handled in a processing line.

The present disclosure also relates to an assembly comprising the abovementioned support device (herein also referred to as "first support device") and a second support device for supporting a plurality of further containers for pharmaceutical use or for supporting a plurality of closure elements configured to close containers for pharmaceutical use, wherein the second support device is placed above the first support device.

BACKGROUND

The support device of the present disclosure meets the definition of "nest" of ISO 21882:2019 standard.

Although explicit reference will be made in this description and the following claims to containers for pharmaceutical use, the support device of the disclosure is also suitable for supporting containers for medical, cosmetic or veterinary use.

For simplicity of discussion, in the present description all the containers that can be supported by the support device of the disclosure are also indicated with the term "primary containers".

Non-limiting examples of primary containers are vials, ampoules, cartridges and syringes.

In the present description and in the appended figures specific reference will be made, as a non-limiting example of primary containers, to the vials.

As known, the primary containers are often handled in the processing lines by aggregating them into a secondary container called "nest".

In accordance with ISO 21882:2019 standard, the nest comprises a plate made of plastic material on which a plurality of housing seats configured to house primary containers are made. These housing seats are distributed in the plate according to a predetermined layout and are shaped so as to stably support the primary containers, keeping them separated from each other and thus avoiding possible mutual collisions.

It is also known to aggregate the primary containers into a so-called "nest and tub" configuration, in which the primary containers are placed inside the housing seats of a nest and the nest is in turn placed inside a tray so-called "tub". This configuration is particularly suitable for supporting and handling the primary containers during the various processing steps to which they are subjected along the processing line, such as washing, packaging, sterilization, filling, capping, crimping, freeze-drying, storage, manual or automated inspection operations, etc.

DE 202016107209 U1 and U.S. Ser. No. 10/207,832 B2 describe examples of nest for vials and for cartridges, respectively.

The Applicant has focused his attention on the process for capping vials previously arranged in a nest. This process provides for the aseptic sealing of the abovementioned vials by applying on each of them a suitable closure element.

In order to allow the simultaneous capping of all the vials placed in the nest, the closure elements are first mounted on a special support device, known as a "cap-nest", and then coupled to the vials placed in the nest after having placed the cap-nest above the nest.

For this purpose, the cap-nest has a plurality of retaining members, each configured to support a respective closure element. These retaining members are distributed in the cap-nest according to a layout identical to that of the housing seats of the nest, so that once the cap-nest is placed above the nest each closure element can be coupled to a respective vial.

Examples of cap-nest are described in WO 2018020505A1.

The Applicant has realized that in order to achieve an effective and easy capping/sealing of the vials placed in the nest through the closure elements arranged in the cap-nest, it is advisable to achieve a precise and stable coupling between nest and cap-nest.

The Applicant has therefore thought to provide the nest with coupling elements suitable to cooperate with respective coupling elements specifically provided in the cap-nest.

The Applicant has thought that the same coupling elements provided in the nest for the coupling with the cap-nest can be used to allow a precise and stable coupling of a nest with a further nest.

The technical problem underlying the present disclosure is to provide a support device for supporting a plurality of containers for pharmaceutical use that allows to achieve a stable and precise coupling of said support device with a support device for supporting closure elements configured to close the abovementioned containers or with another support device for supporting other containers for pharmaceutical use.

SUMMARY

The present disclosure therefore relates, in a first aspect thereof, to a support device for supporting a plurality of containers for pharmaceutical use to be handled in a processing line, said support device having the features recited in claim 1.

In particular, the abovementioned support device comprises a body having an upper surface, a lower surface, a perimeter portion and a central portion delimited by said perimeter portion, wherein said central portion comprises, between said upper surface and said lower surface, a plurality of housing seats configured to house containers for pharmaceutical use and a plurality of separating elements interposed between adjacent housing seats, the support device being characterised in that at least two of said separating elements are hollow and each of said at least two separating elements comprises, at said upper surface, a through opening.

In the present description and in the appended claims, the terms "upper" and "lower", and similar terms such as "above" and/or "below" and/or "over" and/or "under", if present, are used with reference to the position taken by the support device during handling in the processing line of the containers for pharmaceutical use arranged therein.

The provision in the support device of the disclosure of hollow separating elements having an opening at the upper surface of the support device allows the insertion into said hollow separating elements of respective coupling elements having an elongated shape, for example shaped as a pillar, specifically provided in a support device for supporting closure elements configured to close containers for pharmaceutical use or in a further support device for supporting further containers for pharmaceutical use, thus achieving the desired precise and stable coupling between the abovementioned support devices without collisions between the containers housed in two respective stacked support devices.

In a second aspect thereof, the present disclosure relates to an assembly according to claim 10.

In particular, said assembly comprises a support device according to the first aspect of the disclosure (herein also referred to as "first support device") and a second support device for supporting a plurality closure elements configured to close containers for pharmaceutical use or a plurality of further containers for pharmaceutical use, wherein said second support device is placed above the first support device and comprises at least two coupling elements inserted into the through openings of the abovementioned at least two separating elements of the first support device.

The present disclosure can have, in any of the abovementioned aspects, at least one of the preferred features recited in the dependent claims and described below, wherein each of these features can be provided individually or in combination with the other preferred features.

In other innovative aspects thereof, the support device comprises only some of the abovementioned features in combination with one or more of the features described herein below as preferred features.

Preferably, each separating element is interposed between three adjacent housing seats.

More preferably, each separating element defines a first portion of side wall of each of said three housing seats.

In this way, each housing seat is delimited by six adjacent separating elements, with the exception of the housing seats adjacent to the perimeter portion which are delimited by a smaller number of separating elements, being in part also delimited by the abovementioned perimeter portion.

Preferably, each separating element has, at said upper surface, a substantially triangular shape, more preferably with truncated vertices of the triangle and/or curved sides of the triangle.

Preferably, each separating element has, in any cross-section thereof, a substantially triangular shape, more preferably with truncated vertices of the triangle and/or curved sides of the triangle.

Preferably, the abovementioned sides extend along respective arcs of circumference, so as to define for each housing seat a substantially cylindrical side wall. Such housing seats are configured to house containers for pharmaceutical use having circular cross-section.

Preferably, each housing seat comprises a base.

Preferably, said base has a lower face lying on said lower surface and an upper face configured to support a respective container for pharmaceutical use.

Preferably, each housing seat comprises an outer perimeter edge that is raised with respect to said lower surface. Housing seats of this type can also be provided in support devices that do not have hollow separating elements as described above.

The raised outer perimeter edges allow two or more support devices stacked on each other to be stably and precisely coupled.

Preferably, the aforesaid body comprises a plate interposed between said upper surface and said lower surface.

Preferably, said plate has a substantially quadrangular shape, more preferably rectangular.

More preferably, the housing seats and the separating elements extend on opposite sides with respect to said plate.

Preferably, the perimeter edge of the support device is defined in such a plate.

Preferably, said perimeter edge is substantially planar and allows the support device to rest on an inner perimeter edge of a tray or tub.

Preferably, the plurality of housing seats comprises first housing seats adjacent to said perimeter portion.

More preferably, each of the first housing seats comprises a second portion of side wall facing toward said perimeter portion and extended between said lower surface and said upper surface.

Even more preferably, some of the second portions of side wall comprise an opening extended between the plate and said upper surface. Such openings can also be provided in support devices that do not have hollow separating elements as described above.

The abovementioned openings allow the coupling of the support device of the disclosure with a support device for supporting closure elements configured to close the abovementioned containers for pharmaceutical use, or with a further support device for supporting further containers for pharmaceutical use, which has, in a perimeter portion thereof, coupling elements having an elongated shape, for example shaped as a pillar, avoiding risks of interference between said coupling elements and the abovementioned second side wall portions.

Preferably, at least some of the abovementioned second side wall portions comprise at least one recess extended from said lower surface towards the plate. Such recesses can also be provided in support devices that do not have hollow separating elements as described above.

These recesses allow easy insertion and easy removal of the support device into/from the abovementioned tray or tub, avoiding or limiting a possible interference between the inner side wall of the tub and the abovementioned second portions of side wall.

Preferably, two of said recesses are provided in first housing seats that are located at the corners of the plate and a single recess is provided at other first housing seats. The Applicant has in fact found that the housing seats that are located at the corners of the plate are likely to interfere both with an inner side wall of the tub and with the connecting wall between the abovementioned inner side wall and another inner side wall of the tub. It is therefore advisable to provide at said housing seats a greater clearance with respect to the inner side surface of the tub.

In a preferred embodiment, each housing seat is connected to an adjacent housing seat by a respective reinforcing rib. Such reinforcing ribs can also be provided in support devices that do not have hollow separating elements as described above.

The abovementioned reinforcing ribs strengthen both the housing seats and the plate of the support device.

Preferably, each reinforcing rib comprises a first portion extended from the plate towards said lower surface and having a first thickness.

Preferably, each reinforcing rib comprises a second portion extended from said first portion towards said lower surface and having a second thickness that is lower than said first thickness. In this way the extraction of the support device from the mould at the end of its moulding is facilitated.

Preferably, said second portion is arranged at a median plane of said first portion.

Preferably, said second portion extends for a part having a length such that it does not reach said raised outer perimeter edge, so as not to hinder the correct stacking of the support device with a further support device. The stacking height is in fact defined by the depth of the raised outer perimeter edge and it is therefore provided that this outer perimeter edge is not reached so as not to compromise the correct stacking.

These aspects are merely an illustrative aspect of the innumerable aspects associated with the present disclosure and should not be deemed as limiting in any manner. These and other aspects, features and advantages of the present disclosure will become apparent from the following detailed description when taken in conjunction with the referenced figures.

BRIEF DESCRIPTION OF THE DRAWINGS

Further characteristics and advantages of the present disclosure will become apparent from the following detailed description of a preferred embodiment thereof, which is made with reference to the accompanying drawings and given for indicative and non-limiting purposes. In such drawings.

DETAILED DESCRIPTION

Figure 1:
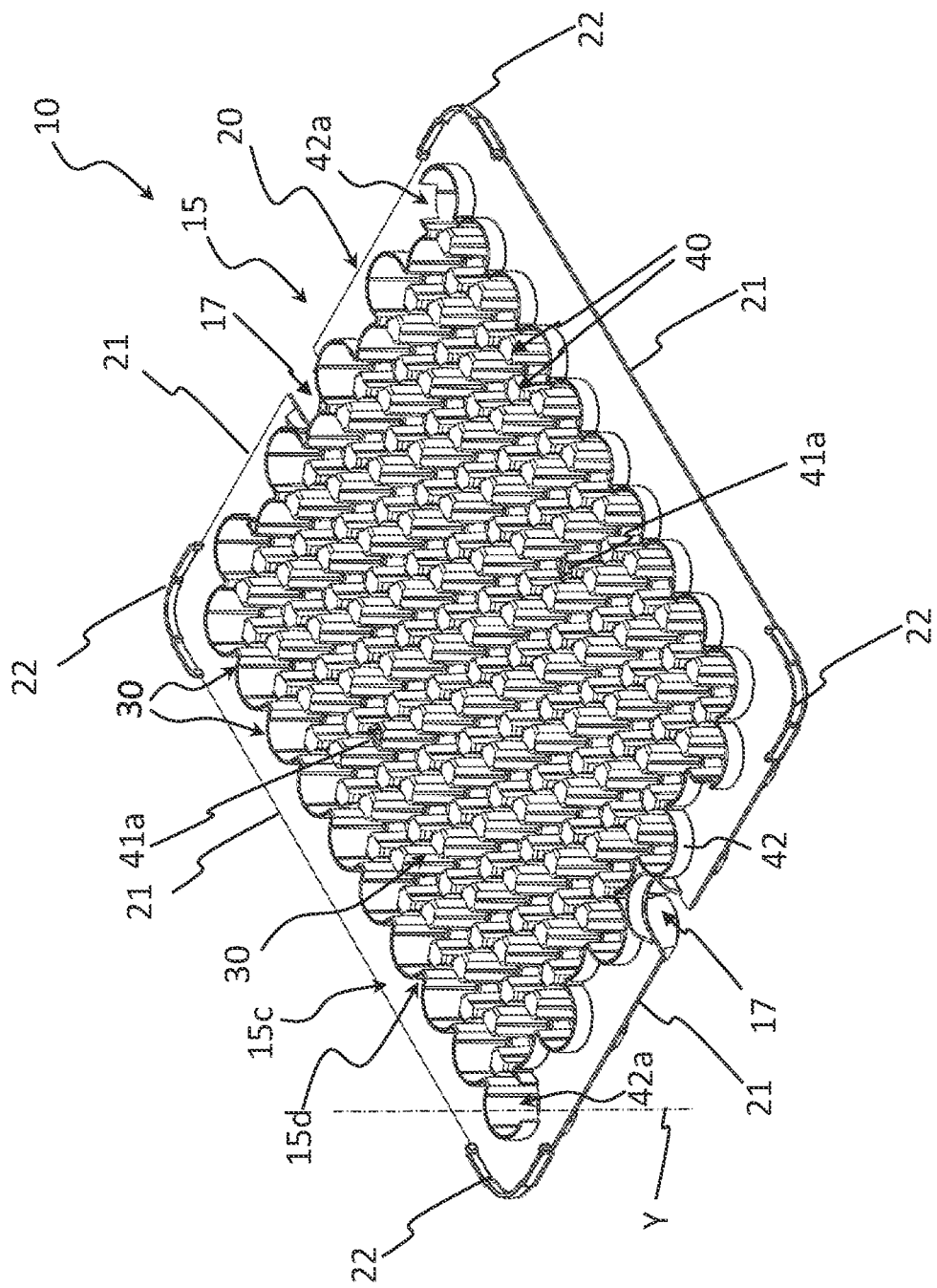
FIG. 1 is a schematic perspective top view of a support device.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

In the following detailed description numerous specific details are set forth in order to provide a thorough understanding of the present disclosure. However, it will be understood by those skilled in the art that the present disclosure may be practiced without these specific details. For example, the present disclosure is not limited in scope to the particular type of industry application depicted in the figures. In other instances, well-known methods, procedures, and components have not been described in detail so as not to obscure the present disclosure.

The headings and sub-headings used herein are intended only for general organization of topics within the present disclosure and are not intended to limit the disclosure of the technology or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Detailed Description" section of this specification are hereby incorporated by reference in their entirety.

In FIGS. 1-7, a support device for supporting a plurality of containers for pharmaceutical is indicated with 10.

These containers are configured to be handled in a processing line (not shown).

In the specific example shown herein, the abovementioned containers are vials 50.

The support device 10 comprises a body 15 having a substantially quadrangular shape. In the non-limiting example described herein, the body 15 is defined by a plate 20 having a substantially rectangular shape. Said plate 20 has four sides 21 and four vertices 22, which are preferably rounded.

Figure 7:
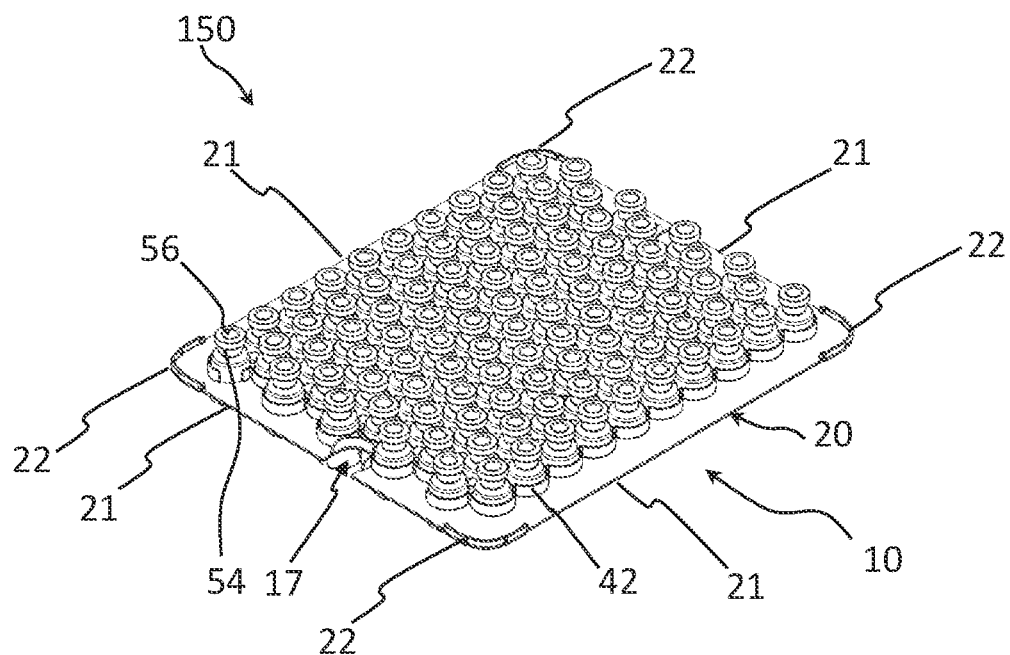
FIG. 7 is a schematic perspective top view of the support device of FIG. 1 in which a plurality of containers for pharmaceutical use are housed.

The plate 20 comprises a plurality of housing seats 30 configured to house respective vials 50, shown in FIG. 7.

The housing seats 30 are distributed in the plate 20 according to a predetermined layout and are shaped so as to stably support the vials 50, keeping them separated from each other and thus avoiding possible mutual collisions.

In the non-limiting example of FIGS. 1-7, the housing seats 30 are arranged in the plate 20 according to a honeycomb or checkerboard configuration (FIG. 5), i.e. wherein each housing seat 30 is surrounded by six adjacent housing seats 30, except for the housing seats 30 adjacent to the sides 21 of the plate 20, hereinafter referred to as "perimeter housing seats 30". In different embodiments, the seats are ordered along a plurality of rows and columns.

The body 15, and hence the plate 20, has a perimeter portion 15c delimited externally by the four sides 21 and by the four vertices 22 of the plate 20, and a central portion 15d delimited by the perimeter portion 15c and comprising the housing seats 30.

Each vial 50 has a substantially cylindrical shape and comprises a substantially circular closed base surface and, on the side opposite to the base surface, a neck 54 provided with a through opening 56 configured to allow the filling of the vial 50 with a predetermined amount of a pharmaceutical product, in the exemplary and non-limiting case of vials 50 for pharmaceutical use.

The vials 50 are typically made of glass or of a thermoplastic material.

With reference to FIG. 7, after having arranged the vials 50 of a production batch in the housing seats 30 of the support device 10, an organized assembly 150 of vials 50 is obtained, that allows the simultaneous processing of all the vials 50 of the production batch. Such processing comprises, inter alia, a step of capping the vials 50.

The latter, once they are arranged in the housing seats 30 of the support device 10, are handled along a processing line (not shown) by moving the support device 10. At least part of this handling is carried out after having inserted the support device 10 into a tub 200 shown in FIG. 8.

To this end, the perimeter portion 15c of the plate 20 comprises a pair of opposite through slots 17 configured to facilitate the insertion and the extraction of the support device 10 into/from the tub 200.

Figure 8:
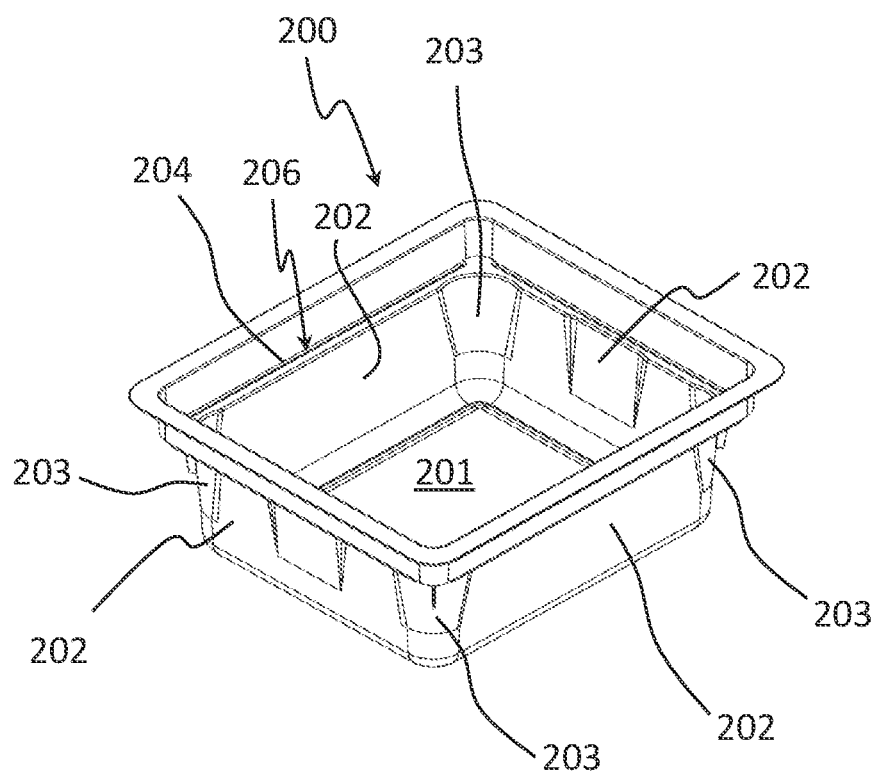
FIG. 8 is a schematic perspective view of a tub configured to house the support device of FIG. 1.

In the non-limiting example of FIG. 8, the tub 200 has a substantially parallelepipedal or truncated-pyramidal shape and comprises a substantially flat bottom surface 201 and four substantially flat side walls 202 that are connected two by two by respective connecting walls 203.

An inner perimeter edge 206 extends from the inner faces of the side walls 202 and of the connecting walls 203 inwardly in the tub 200. This inner perimeter edge 206 defines an abutment surface 204 on which the perimeter portion 15c of the plate 20 is intended to rest when the support device 10 is placed inside the tub 200. The inner perimeter edge may be replaced by a plurality of ribs extending from the inner faces of the side walls and/or connecting walls, each rib comprising a rest surface defining a respective abutment surface on which the perimeter portion 15c of the plate 20 is intended to be rested.

Once the vials 50 of a production batch are inserted into the housing seats 30 of the support device 10 and the latter is inserted into the tub 200, an aggregation configuration of the vials 50 known as "nest and tub" is made, in which the support device 10 is the "nest" and the tub 200 is the "tub".

The housing seats 30 extend on opposite sides of the plate 20 between a lower surface 15a arranged below the plate 20 and an upper surface 15b arranged above the plate 20.

The lower surface 15a is substantially flat and is defined at the lower ends 31a of the housing seats 30.

The upper surface 15b is also substantially flat and is defined at the upper ends 31b of the housing seats 30.

Figure 4:
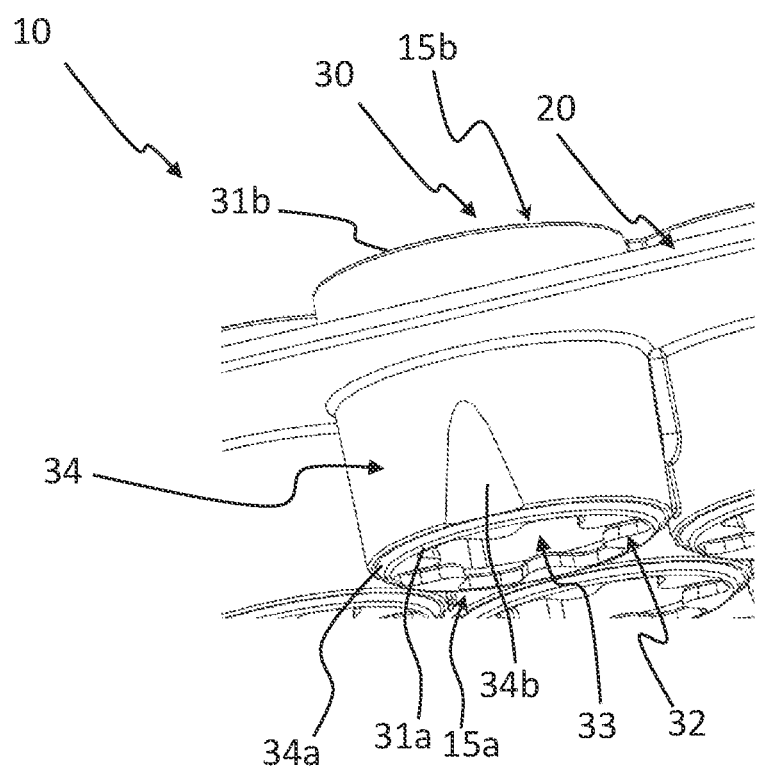
FIG. 4 is a schematic perspective view on an enlarged scale of a further portion of the support device of FIG. 1.

As shown for example in FIG. 4, each of the housing seats 30 comprises, at the lower end thereof 31a, a base 32 having a through opening 33 and, at the upper end thereof 31b, a through opening configured to allow the insertion and the extraction of a respective vial 50.

The base 32 has a predetermined thickness measured between a lower face of the base 32 that is configured to rest on a substantially horizontal operating surface of the processing line and that lies on the abovementioned lower surface 15a, and an upper face of the base 32 that is configured to support the vial 50.

Each housing seat 30 further comprises a side wall 34 which, in the non-limiting example of FIGS. 1-7, delimits a substantially cylindrical space configured to receive the vial 50.

The side wall 34 extends starting from the base 32 up to the upper surface 15b of the plate 20 along a longitudinal axis Y that is substantially orthogonal to the plate 20.

In the non-limiting example of FIGS. 1-7, the base 32 is defined by six rest elements 32a projecting radially from the side wall 34 inwardly in the housing seat 30 and circumferentially equally spaced from each other, in particular arranged angularly offset by 600 from each other around the longitudinal axis Y. In other embodiments not shown, the rest elements are four and are angularly offset from each other by 90° or three and are angularly offset from each other by 120°.

Figure 3:
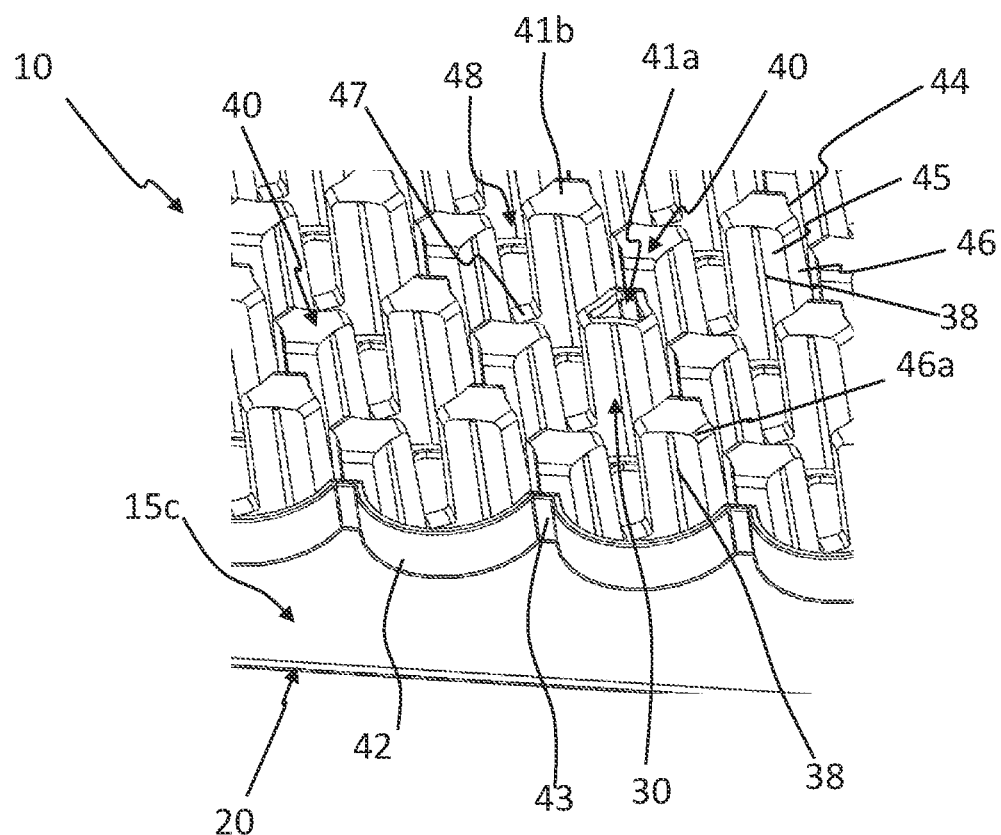
FIG. 3 is a schematic perspective view on an enlarged scale of a side portion of the support device of FIG. 1.
Figure 6:
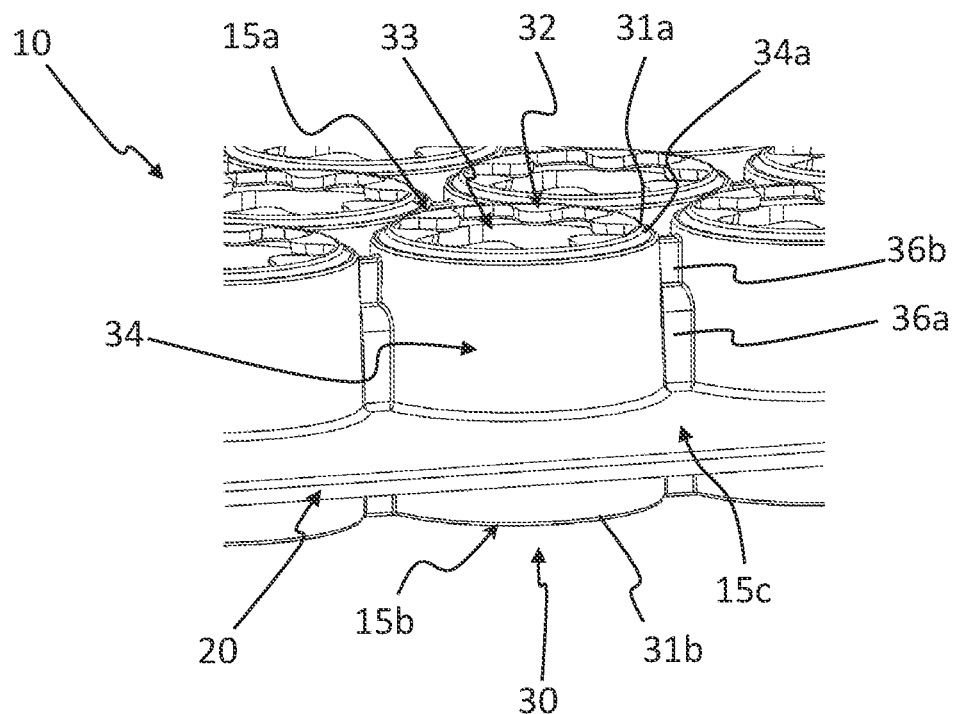
FIG. 6 is a schematic perspective bottom view and on an enlarged scale of a further portion of the support device of FIG. 1.

As shown for example in FIG. 3, the side wall 34 of the housing seats 30 other than the perimeter housing seats 30 is defined by separating elements 40 interposed between adjacent housing seats 30. As shown in FIGS. 1, 3 and 6, each of these housing seats 30 is surrounded by six separating elements 40.

Differently, the side wall 34 of the perimeter housing seats 30 is only partly defined by separating elements 40 interposed between adjacent housing seats 30, another part of said side wall 34 being in fact defined by a respective substantially cylindrical portion 42 of a wall that separates the perimeter portion 15c of the plate 20 from the central portion 15d of the plate 20.

The separating elements 40 are therefore provided in the central portion 15d and, like the housing seats 30, extend between the lower surface 15a and the upper surface 15b.

Each separating element 40 is interposed between three adjacent housing seats 30 and comprises a plurality of sides 44 each defining a portion of side wall 34 of each of the three housing seats 30.

Each separating element 40 is substantially prismatic in shape with a substantially triangular cross-section.

As shown in FIG. 3, the three sides 44 of each separating element 40 are curved and extend, in any cross-section of the separating element 40, according to respective arcs of circumference. Each of the three sides 44 thus defines a portion 45 of side wall 34 of substantially cylindrical shape.

The three vertices of the triangle defined in any cross-section of the separating element 40 are truncated, so as to define at each of the abovementioned vertices a respective substantially flat wall 46. Between two facing walls 46 of two adjacent separating elements 40 a groove 48 is provided, such a groove having a bottom surface 47 that is raised with respect to the lower surface 15a of the plate 20.

Two of the separating elements 40 are hollow and have, at the upper surface 15b of the plate 20, a through opening 41a. The other separating elements 40 are also hollow but are closed at the upper surface 15b, each by a respective top wall 41b having a shape similar to that described above with reference to the cross-section of the separating element 40.

The through opening 41a has a shape similar to that of the top walls 41b.

Between the top wall 41b, or the through opening 41a, and each of the three walls 46 of the separating element 40 a respective inclined wall 46a is provided.

The through opening 41a allows the insertion into the cavity of the two abovementioned separating elements 40 of a respective coupling element provided for example in a support device for supporting closure elements configured to close vials 50, also called cap-nest, or in a further support device for supporting a plurality of further vials for pharmaceutical use.

As shown for example in FIG. 3, the portions 42 of the perimeter housing seats 30 are connected to each other by connecting portions 43 extending above the plate 20.

With reference to FIG. 1, in the portion 42 of some perimeter housing seats 30 a through opening 42a is formed that extends between the plate 20 and the upper surface 15b and that faces toward the perimeter portion 15c.

The through opening 42a allows an undesired interference with a further coupling element provided in the "cap-nest" or in the abovementioned further support device to be avoided.

In the non-limiting example shown in FIG. 1, the through openings 42a are provided in portions 42 of four perimeter housing seats 30 arranged at the four corners of the central portion 15d of the plate 20.

As shown in FIG. 4, the side wall 34 of each housing seat 30 comprises, at the lower end 31a, an outer perimeter edge 34a that is raised with respect to the lower surface 15a. Said outer perimeter edge 34a defines, at each housing seat 30, a step that allows stacking the support device 10 on another support device of the same type.

Figure 2:
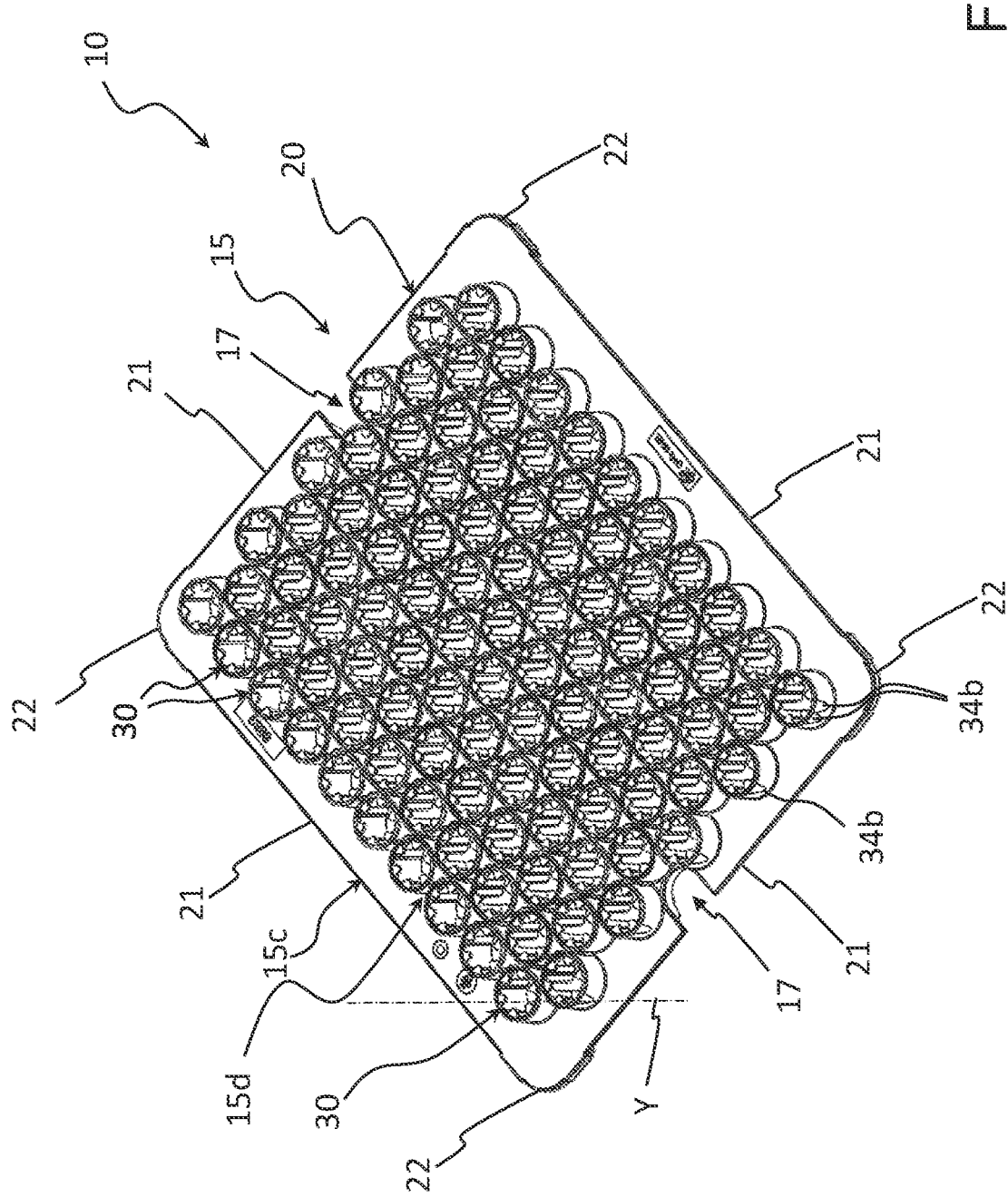
FIG. 2 is a schematic perspective bottom view of the support device of FIG. 1.

As shown in FIGS. 2 and 4, a recess 34b is provided on the side wall 34 of some of the perimeter housing seats 30. Said recess 34b extends from the lower surface 15a towards the plate 20, without reaching the latter.

The recess 34b is facing outwardly from support device 10 so as to face one of the side walls 202 or of the connecting walls 203 of the tub 200, when the support device 10 is inserted into the tub 200.

Two recesses 34b (FIG. 2) are provided in the perimeter housing seats 30 that are located near the vertices 22 of the plate 20.

Figure 5:
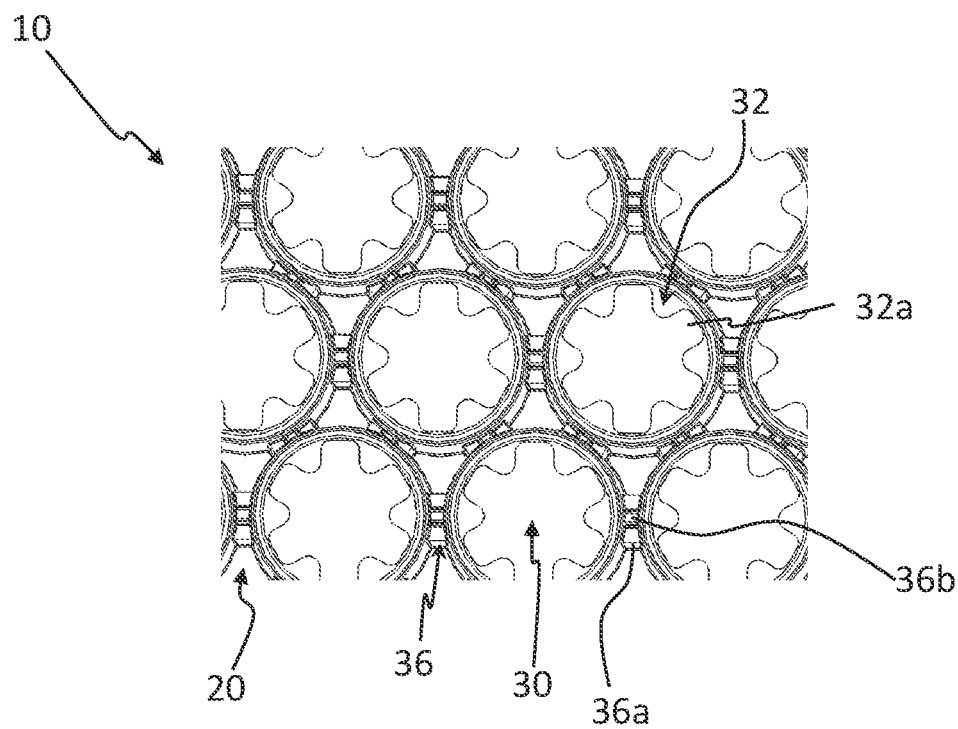
FIG. 5 is a schematic plan bottom view and on an enlarged scale of a central portion of the support device of FIG. 1.

As shown in FIGS. 5 and 6, a reinforcing rib 36 extends externally to each housing seat 30 from the side wall 34 of said housing seat 30 up to the side wall 34 of a housing seat 30 adjacent thereto so as to connect the two housing seats 30.

The reinforcing ribs 36 extend from the plate 20 towards the lower surface 15a.

In particular, each reinforcing rib 36 comprises a first portion 36a extended from the plate 20 towards the lower surface 15a and a second portion 36b extended from the first portion 36a towards the lower surface 15a. The second portion 36b has a thickness that is lower than the thickness of the first portion 36a and is located centrally with respect to the first portion 36a, i.e. at a median plane of the first portion 36a.

The second portion 36b extends for a part having a length such that it does not reach the lower surface 15a. More particularly, each second portion 36b does not reach the raised outer perimeter edges 34a of the housing seats 30. In this way it is possible to stack the support device 10 on a further support device of the same type.

In order to allow centering the vials 50 within the respective housing seats 30, each housing seat 30 comprises a plurality of longitudinal ribs 38 projecting from the respective side wall 34 inwardly in the housing seat 30.

In the non-limiting example of FIGS. 1-7, the longitudinal ribs 38 are six, have the same shape and dimensions as each other, are circumferentially equally spaced from each other, and are arranged above the rest elements 32a. In particular, the longitudinal ribs 38 extend from the sides 44 of the separating elements 40. More specifically, each longitudinal rib 38 is arranged at the centre of the respective side 44. Thus, three longitudinal ribs 38 are formed on each separating element 40, one for each of the three housing seats 30 adjacent to the separating element 40 itself.

The plate 20 of the support device 10 described above can be made by moulding plastic material, for example polypropylene.

The preferred embodiments of the disclosure have been described above to explain the principles of the present disclosure and its practical application to thereby enable others skilled in the art to utilize the present disclosure. However, as various modifications could be made in the constructions and methods herein described and illustrated without departing from the scope of the present disclosure, it is intended that all matter contained in the foregoing description or shown in the accompanying drawings, including all materials expressly incorporated by reference herein, shall be interpreted as illustrative rather than limiting. Thus, the breadth and scope of the present disclosure should not be limited by the above-described exemplary embodiment but should be defined only in accordance with the following claims appended hereto and their equivalents.

What is claimed is:

1. A support device for supporting a plurality of containers for pharmaceutical use to be handled in a processing line comprising:
    a body having an upper surface, a lower surface, a perimeter portion and a central portion delimited by said perimeter portion,
    wherein the central portion comprises between the upper surface and the lower surface:
        a plurality of housing seats configured to house the plurality of containers; and
        a plurality of separating elements interposed between adjacent housing seats;
        wherein at least two of the plurality of separating elements are hollow;
        wherein each of the at least two hollow separating elements has a through opening at the upper surface; and
        wherein the other of the plurality of separating elements are hollow and are closed at the upper surface.

2. The support device of claim 1, wherein each separating element is interposed between three adjacent housing seats and the separating element defines a first portion of a side wall of each of the three housing seats.

3. The support device of claim 1, wherein the upper surface and any cross-section of each separating element comprises a triangular shape, wherein vertices of the triangular shape are truncated and sides of the triangular shape are curved.

4. The support device of claim 1, wherein each of the plurality of housing seats comprises:
    a base having a lower face contacting the lower surface of the body;
    an upper face; and
    an outer perimeter edge that is raised with respect to the lower surface.

5. The support device of claim 1, wherein the body further comprises a plate interposed between the upper surface and the lower surface and wherein the plurality of housing seats and the plurality of separating elements extend on opposite sides with respect to the plate.

6. The support device of claim 5, wherein the plurality of housing seats comprises at least one first housing seat that is adjacent to the perimeter portion and the at least one first housing seat having a second portion of side wall facing toward the perimeter portion and extending between the lower surface and the upper surface.

7. The support device of claim 6, wherein the second portion of side wall of the at least one first housing seat comprises an opening extending between the plate and the upper surface.

8. The support device of claim 6, wherein the second portion of side wall of the at least one first housing seat comprises at least one recess extending from said lower surface towards said plate.

9. The support device of claim 4, wherein each housing seat is connected with an adjacent housing seat by a respective reinforcing rib, wherein each respective reinforcing rib comprises:
    a first portion extending from the plate towards the lower surface and having a first thickness;
    a second portion extending from the first portion towards the lower surface and having a second thickness that is less than the first thickness;

wherein the second portion is arranged at a median plane of the first portion and extends towards but does not reach the outer perimeter edge.

10. An assembly comprising:

the support device for supporting a plurality of containers for pharmaceutical use to be handled in a processing line according to claim 1; wherein the support device is a first support device;

a second support device for supporting a plurality of elements configured to close the plurality of containers or a plurality of further containers for pharmaceutical use, the second support device comprising at least two coupling elements configured for insertion into the through opening of the at least two separating elements.

* * * * *